United States Patent [19]
Cappel et al.

[11] Patent Number: 5,143,728
[45] Date of Patent: Sep. 1, 1992

[54] PSYLLIUM-CONTAINING FILLING COMPOSITIONS AND METHODS

[75] Inventors: James W. Cappel, Fairfield, Ohio; Robert D. Rece, Edgewood, Ky.

[73] Assignee: The Proctor & Gamble Company, Cincinnati, Ohio

[21] Appl. No.: 700,090

[22] Filed: May 1, 1991

Related U.S. Application Data

[63] Continuation of Ser. No. 492,220, Mar. 13, 1990, abandoned, which is a continuation of Ser. No. 83,441, Sep. 4, 1987, abandoned.

[51] Int. Cl.$^5$ .............................................. A61K 35/78
[52] U.S. Cl. ............................ 424/195/00; 514/866; 514/892
[58] Field of Search ..................... 424/191.1; 514/866, 514/892

[56] References Cited

U.S. PATENT DOCUMENTS

| | | | |
|---|---|---|---|
| 3,148,114 | 9/1964 | Fahrenback | 424/198.1 |
| 4,321,263 | 3/1982 | Powell et al. | 524/892 |
| 4,341,807 | 7/1982 | Turbak et al. | 426/570 |
| 4,565,702 | 1/1986 | Morley et al. | 426/93 |
| 4,639,367 | 1/1987 | Mackles | 514/945 |
| 4,698,232 | 10/1987 | Shae et al. | 426/575 |

FOREIGN PATENT DOCUMENTS 1446644 6/1985 European Pat. Off. .

OTHER PUBLICATIONS

Naturacel ® Manufactured by Mead Johnson Natural Division 1983
Anderson, et al. Fed/ Proc. 46:877, 1987.
Anderson, et al. Am. J. Gast. 81:907–919, 1986.
Faberberg Curr. Ther. Res. 31:166, 1982.

*Primary Examiner*—John W. Rollins
*Attorney, Agent, or Firm*—Kim William Zerby; Douglas C. Mohl; Richard C. Witte

[57] ABSTRACT

Psyllium-containing filling compositions having excellent texture, mouthfeel, and palatability. These filling compositions essentially comprise psyllium fiber and higher levels of glycerin, and preferably comprise sweeteners and flavorants. Furthermore, they have water activities ("$A_W$") below about 0.35. The compositions are ingested to control constipation, bowel function, blood cholestrol levels, glood glucose tolerance, and/or appetite, as well as for prophylaxis and treatment of intestinal disorders.

12 Claims, No Drawings

PSYLLIUM-CONTAINING FILLING COMPOSITIONS AND METHODS

This is a continuation of application Ser. No. 07/492,220 filed Mar. 13, 1990, now abandoned, which is a continuation of application Ser. No. 07/083,441 Sep. 4, 1987, now abandoned.

BACKGROUND OF THE INVENTION

The present invention relates to novel high fiber edible products having a psyllium-containing filling. These products have excellent texture, mouthfeel, and palatability. They are useful as dietary aids in the control of bowel function, constipation, blood cholesterol levels, blood glucose tolerance, and/or appetite, as well as prophylaxis and treatment of intestinal disorders.

Psyllium-containing products are currently widely used for laxation. In addition, recent research has demonstrated the effectiveness of psyllium fiber in reducing human serum cholesterol levels, and in controlling blood glucose levels in diabetics. See, for example, J. W. Anderson, et al., *Fed. Proc.*, 46, 877 (1987); J. W. Anderson, et al., *Am. J. Gastroenterol.*, 81, 907–919 (1986); and S. Faberberg, *Curr. Ther. Res.*, 31, 166 (1982); all being incorporated herein by reference in their entirety.

The commercial psyllium-containing products typically require the user to mix small particle size psyllium (e.g., psyllium mucilloid) with a liquid. The user then drinks the prepared suspension. Such products may not be convenient to use in all situations. Furthermore, palatability of psyllium-containing products vary depending on the form used, and, of course, the user's particular preference. Frequently, however, psyllium-containing products are viewed as having poor palatability. Improving the palatability of psyllium-containing products is therefore a continuing need which would benefit a significant number of consumers. The use of more palatable products might result in improved compliance for dosing regimens involving several doses or extended duration therapy. Thus, while psyllium can be (and in fact has been) combined with many carriers and flavorants in many forms, there continues to be a need for new, useful, convenient, and highly palatable psyllium-containing products.

Attempts at improving the aesthetics (and ease of preparation) of psyllium-containing products have generally heretofore focused on adding sugar and/or flavor to smaller particle size psyllium. However, simply adding psyllium fiber to any carrier material typically results in an unacceptable product. For example, adding psyllium fiber (in amounts sufficient to provide therapeutic benefits) to a typical fruit filling results in an unacceptably gummy, chewy filling. This appears to result from the psyllium fibers being hydrated by the water present in the typical filling compositions. Attempts at solving the gummy texture by reducing the water content of the filling sufficient to prevent hydration of the psyllium fibers cures that problem. However, this results in an equally unacceptable filling from the standpoint of mouthfeel, creating a product that tastes very dry and is hard to swallow. Thus, there was no entirely satisfactory solution to this dilemma before the present invention.

It is therefore an object of the present invention to provide highly palatable, psyllium-containing filling compositions. Another object is to provide convenient, portable psyllium-containing compositions which do not require mixing by the consumer prior to use. A further object is to provide psyllium-containing compositions having excellent texture, mouthfeel, and palatability. A further object is to provide a highly palatable psyllium-containing composition with improved consumer acceptance to enhance compliance with a high fiber diet. An object of the present invention is also to provide high fiber diets. Finally, objects of the present invention are to provide methods for producing laxation and regulating bowel function; methods for reducing serum cholesterol levels in subjects with elevated cholesterol levels; and methods for controlling blood glucose levels in diabetics.

These and other objects of the present invention will become readily apparent from the detailed description which follows.

All percentages and ratios used herein are by weight unless otherwise specified.

SUMMARY OF THE INVENTION

The present invention relates to psyllium-containing filling compositions. These compositions comprise: (1) from about 1% to about 50% of psyllium fiber; (2) from about 10% to about 75% of glycerin; (3) from about 0% to about 80% of at least one sweetener; and (4) from about 0% to about 10% of at least one flavorant. These compositions have low water activities, being about 0.35 or less.

The present invention further relates to methods for providing laxation and bowel regulation; methods for reducing serum cholesterol levels; and methods for controlling blood glucose levels. All methods comprise orally administering to a human in need of such treatments a safe and effective amount of a psyllium-containing composition of the present invention.

DETAILED DESCRIPTION OF THE INVENTION

Psyllium-Containing Filling Compositions

The present invention is psyllium-containing filling compositions. These compositions have low water activities ("$A_w$") of about 0.35 or less, preferably from about 0.05 to about 0.3, and more preferably from about 0.1 to about 0.25. The compositions essentially comprise: (a) psyllium fiber; and (b) glycerin. Preferred optional components are at least one sweetener (preferably part of which is sorbitol), and at least one flavorant.

As noted hereinbefore, the compositions of the present invention essentially have low $A_w$. In order to maintain low $A_w$ of the compositions, and to avoid hydrating the psyllium fibers even at this low $A_w$, the compositions should not be exposed to high temperatures for extended periods of time (e.g., as typically occur during baking) and they should not be combined into products wherein the compositions herein are stored for extended periods in contact with materials having $A_w$'s greater than about 0.3 (preferably the $A_w$ is less than about 0.2, and more preferably the $A_w$ is less than about 0.1). Such contact will increase the $A_w$ of the filling composition during storage. For example, a sandwich cookie according to the present invention comprises a filling composition herein sandwiched between two cookie basecakes having an $A_w$ of less than about 0.3, preferably less than about 0.2, and more preferably less than about 0.1. It is, however, envisioned that compositions herein can be combined in contact with materials having higher $A_w$ when ingestion of the combination will occur before the $A_w$ of compositions herein increases beyond acceptable levels.

$A_w$ is a well-known property in the art (see, for example, "Water Activity and Food" by Troller and Christian (Academic Press, N.Y.; 1978) incorporated by reference herein in its entirety). Measurement of the $A_w$ of the compositions herein is achieved by using commercially available instruments sold for the purpose of measuring $A_w$ (for example, the "Rotronic Hygroskop DT", sold by Kaymont Instrument Corporation, Huntington Station, N.Y., and the Operating Instructions therefor which are incorporated herein by reference).

The filling compositions of the present invention may be used as a spread, e.g., for toast or crackers, or as a topping for desserts. It also may be coated with a coating, such as chocolate, or used as the filling for a sandwich-type cookie. These uses and product forms are simply illustrative of many which are possible for the compositions of the present invention.

The essential and optional components, and the amounts utilized, in the filling compositions according to the present invention are described in detail hereinafter.

(a) Psyllium Fiber:

The psyllium fibers used in the practice of this invention come from psyllium seed, from plants of the Plantago genus. Various species such as *Plantago lanceolate*, *P. rugelii*, and *P. major*, are known. Commercial psyllium includes the French (black; *Plantago indica*), Spanish (*P. psyllium*) and indian (blond; *P. ovata*). Indian (blond) psyllium is preferred for use herein.

The psyllium fiber is obtained from the seed coat. Intact or macerated seeds can be used in the practice of this invention. However, it is typical to remove the seed coats from the rest of the seed by, for example, slight mechanical pressure, and then to use only the seed coat. In the practice of the present invention, it is convenient and desirable to use macerated seed coats in the final composition. The seed coat is therefore preferably removed and sanitized by methods known in the art (preferably with ethylene oxide) prior to use in the present compositions. Furthermore, the psyllium fiber utilized has high purity, preferably being about 85% to about 100% pure, and more preferably being about 95% to about 100% pure.

The compositions of the present invention comprise from about 1% to about 50% psyllium fiber, preferably from about 5% to about 40%, and more preferably from about 20% to about 35%, by weight of the compositions.

(b) Glycerin:

Another essential component of the compositions of the present invention is glycerin at higher concentration levels. Levels greater than about 10% by weight of the compositions are necessary in order to obtain the lubricious, highly palatable character and filling consistency for compositions of the present invention. Higher levels are utilized according to the desired fluidity of the composition. Food grade quality glycerin is commercially available.

Glycerin comprises from about 10% to about 75% of the compositions herein, preferably from about 10% to about 50%, and more preferably from about 10% to about 25%, by weight of the compositions.

(c) Sweeteners:

The compositions herein also preferably comprise at least one sweetner. Preferred sweetners are carbohydrates (e.g., glucose; fructose; sucrose; mannose; lactose), sweet tasting carbohydrate derivatives (e.g., sorbitol; mannitol), and artificial sweeteners (e.g., aspartame; saccharin). More preferred are monosaccharides (especially glucose and fructose), sorbitol, aspartame, and mixtures thereof. Most preferred is at least part of the sweetener comprising sorbitol.

For purposes of the present invention, it is possible to substitute an artificial sweetener (e.g., aspartame, sold as Nutrasweet ® brand sweetener by G. D. Searle; saccharin; cyclamate) for some or all of the sweetener component of the compositions herein. This substitution is particularly preferred when the present composition is to be taken by persons on a restricted caloric diet, or is to be taken by diabetics in order to control blood glucose levels. Examples of artificial sweeteners include saccharin, cyclamate, acesulfame K (American Hoechst), Gem Sweet (Cumberland Packing Corp.), L-sugars (Lev-O-Cal Biospherics), Hernandulcin (University of Illinois), Alitame (Pfizer), Thaumatins, trichloro sucrose, Rebaudioside A, L-aspartyl-L-phenylalanine methyl ester, aspartyl-D-valine isopropyl ester, aspartyl amino malonates, dialkyl aspartyl aspartates, stevioside, glycyrrhizin, p-phenetylurea, 5-nitro-2-propoxyaniline and neohesperidin dihydrochalcone. The term L-aspartyl-L-phenylalanine methyl ester and methyl L-aspartyl-L-phenylalanine are used interchangeably and correspond to the compound also known as aspartame. Preferred artificial sweeteners are saccharin, cyclamate, acesulfame K, and especially aspartame.

The compositions of the present invention preferably comprise in total from about 0% to about 80% of at least one sweetener, more preferably from about 20% to about 65%, and most preferably from about 40% to about 55%, by weight of the compositions. It is further preferred that the sweetener comprise sorbitol in an amount of from about 0% to about 40%, more preferably from about 5% to about 30%, and most preferably from about 10% to about 25%, by weight of the compositions. If one or more artificial sweeteners are present, they preferably comprise in total from about 0.1% to about 80%, and more preferably from about 1% to about 60%, by weight of the compositions.

(d) Flavorants:

The compositions herein also preferably comprise at least one flavorant material. Flavorants may be natural (e.g., fruit puree; natural fruit flavors; natural food flavoring oils such as peppermint oil) or artificial (e.g., artificial fruit flavors). If natural flavorants are utilized, it is important to limit the water content of such flavorants such that the compositions herein are formulated having the required low $A_W$.

The compositions herein preferably comprise in total from about 0% to about 10% of at least one flavorant, and more preferably from about 0.1% to about 7%, by weight of the compositions.

(e) Additional Optional Components:

The compositions herein may further comprise other optional components selected according to the properties desired for the composition. For example, the compositions herein may comprise thickeners (e.g., pectins; gums), preservatives, flavor enhancers, colorants, essences, fruits, and nut meats. Bulking agents may also be added such as malt soup extract, methyl cellulose, polycarbophil, calcium polycarbophil, carboxymethyl cellulose, and bran fibers (e.g., wheat; oat; corn). Pharmaceutical actives such as stimulants, antispasmodics, topical anesthetics, and anti-inflammatories are further optional components. Selection of these and other optional materials are readily made by one skilled in the art.

METHODS OF TREATMENT

The present invention also relates to a method for providing laxation and regulating bowel function for a human in need of such treatment. This method comprises administering to a human in need of such treatment a safe and effective amount of a psyllium-containing composition of the present invention. Ingestion of from about 2.5 grams to about 30 grams per day of the psyllium fiber in a composition according to the present invention is appropriate in most circumstances to produce laxation. However, this can vary with the size and condition of the patient, and such matters will, of course, be apparent to the attending physician. However, since the psyllium material is non-toxic, even higher ingestion levels can be used without undue side effects. A typical dose for laxation purposes involves administering from about 3 to about 15 grams of psyllium fiber in one dose.

The present invention further relates to methods for reducing serum cholesterol levels in humans. These methods comprise orally administering to a human in need of having a lowered blood cholesterol level a safe and effective amount of a psyllium-containing composition of the present invention. Ingestion of compositions of the present invention comprising amounts sufficient to administer from about 2.5 grams to about 30 grams per day of psyllium fiber, preferably from about 5 grams to about 15 grams, is appropriate in most circumstances. However, this can vary with the size and condition of the patient, and the patient's blood cholesterol level. Such matters will, of course, be apparent to the attending physician. However, since the psyllium material is non-toxic, even higher ingestion levels can be used without undue side effects, keeping in mind that the materials herein have the hereinbefore noted laxative effect.

Treatment of the patient to reduce serum cholesterol levels comprises chronic ingestion in order to lower and maintain the low cholesterol levels. Daily ingestion is preferred, and a daily ingestion of from about 5 grams to about 15 grams of the psyllium fiber is most commonly used, with said ingestion preferably being at two or three regularly spaced intervals throughout the day. Again, depending on the patient's size and cholesterol level in the patient's blood, this can be varied.

The present invention further relates to methods for controlling blood glucose levels in humans. These methods comprise orally administering to a human in need of controlling blood glucose levels a safe and effective amount of a psyllium-containing composition of the present invention, preferably a composition containing artificial sweeteners. Ingestion of compositions of the present invention comprising amounts sufficient to administer from about 2.5 grams to about 30 grams per day of psyllium fiber, preferably from about 5 grams to about 15 grams, is appropriate in most circumstances. However, this can vary with the size and condition of the patient. Such matters will, of course, be apparent to the attending physician. However, since the psyllium material is non-toxic, even higher ingestion levels can be used without undue side effects, keeping in mind that the materials herein have the hereinbefore noted laxative effect.

Treatment of the patient to control blood glucose levels comprises chronic ingestion in order to maintain the desired blood glucose level. Daily ingestion is preferred, and a daily ingestion of from about 5 grams to about 15 grams of the psyllium fiber is most commonly used, with said ingestion preferably being just prior to each meal. Again, depending on the patient's size and condition, this can be varied.

The following examples further describe and demonstrate embodiments within the scope of the present invention. The examples are given solely for the purpose of illustration and are not to be construed as limitations of the present invention as many variations thereof are possible without departing from the spirit and scope.

EXAMPLE I

Psyllium-Containing Apple Filling

A psyllium-containing apple filling composition according to the present invention is prepared having the following components:

| Component | Weight % |
| --- | --- |
| Sorbitol | 15.35 |
| Dextrose | 15.35 |
| Crystalline Fructose | 18.43 |
| Glycerin | 13.21 |
| Psyllium Fiber | 30.71 |
| Citric Acid | 0.25 |
| Malic Acid | 0.25 |
| Apple Puree with Essence[1] | 6.45 |

[1]Supplied by The J. M. Smucker Company; light apple puree concentrate having 33.0° Brix (as determined by refractometer).

This composition is prepared as follows. The sorbitol, dextrose, crystalline fructose, and glycerin are combined and heated to 240° F. in a microwave. The resulting mixture is allowed to cool to 180° F., and then the psyllium fiber is stirred into the mixture. Finally, the citric acid, malic acid, and apple puree are added and stirred to form a homogeneous filling composition according to the present invention. This composition has an $A_w$ of 0.296.

Spreading 12 grams (approximately 1 tablespoon) of this filling composition on crackers or toast and ingesting provides effective laxative benefits to a person in need of laxation. Also, consumption of this filling composition as described two times a day for one month by a person diagnosed as having elevated blood cholesterol levels reduces the person's serum cholesterol level. This filling composition is convenient to use as a spread and has excellent palatability, mouthfeel, taste and texture.

EXAMPLE II

Cookie With Psyllium-Containing Apple Filling

Cookies having a psyllium-containing apple filling (which is prepared as described in Example I) are made as follows.

Cookie basecakes are prepared having the following components:

| Component | Weight % |
| --- | --- |
| Crystalline Fructose | 0.75 |
| Diamond 77 Molasses[1] | 1.0 |
| Water | 5.0 |
| Extra-Fine Sodium Bicarbonate | 0.2 |
| Medium Hardened Vegetable Shortening | 18.0 |
| Sugar | 26.0 |
| Flour | 28.27 |

| Component | Weight % |
| --- | --- |
| Oats | 20.50 |
| Cinnamon | 0.25 |
| Butter | 0.01 |
| Vanilla | 0.02 |

[1] Supplied by Ingredient Technology Corp.

The dough is prepared as follows. Weight into a Hobart mixer (Model No. C-100) bowl the appropriate amounts of crystalline fructose, Diamond 77 molassas, water (70° F.) and extra-fine sodium bicarbonate, and mix for three minutes at speed 2. The appropriate amount of melted shortening (120° F.) is added, and mixed for two minutes at speed 2. Following this, one-half the total amount of sugar is added and mixed for one minute at speed 1. Blended flour, oats, cinnamon, butter, and vanilla are added and mixed for one minute at speed 1. The remaining sugar is then added and the dough mixed at speed 1 for one minute. The dough is then rolled out with a rolling pin to approximately 0.125 inches (3.2 mm) thick, cut using a 55 mm die, and then baked on baking sheets for approximately 9 minutes at 375° F. The resulting basecakes weigh approximately 9 grams, are approximately 2.3 inches (59 mm) in diameter and 0.23 inches (5.9 mm) thick, and have an $A_w$ of less than about 0.1.

The finished psyllium-containing apple filling sandwich cookie is prepared by spreading about 11.2 grams of the psyllium-containing apple filling according to the present invention on a basecake, and then placing another basecake on top. The basecakes are compressed together to distribute the filling evenly between the basecakes.

Consumption of one of these compositions daily by a person in need of laxation provides effective laxative benefits and regulates bowel function. Furthermore, consumption of one of these compositions three times a day for one month by a person diagnosed as having moderate hypercholesterolemia or elevated blood cholesterol levels reduces the person's serum cholesterol level. These cookies are convenient to use and provide psyllium in a very palatable form.

EXAMPLE III

Psyllium-Containing Raspberry Filling

A psyllium-containing filling composition according to the present invention is prepared having the following components:

| Component | Weight % |
| --- | --- |
| Sorbitol | 15.38 |
| Dextrose | 15.38 |
| Crystalline Fructose | 18.46 |
| Glycerin | 15.23 |
| Psyllium Fiber[1] | 30.76 |
| Citric Acid | 0.25 |
| Malic Acid | 0.25 |
| Raspberry Essence[2] | 0.14 |
| Raspberry Puree[2] | 6.16 |

[1] Psyllium fiber having the following particle size distribution: 1% on 16 mesh (U.S. Standard); 51% through 16 on 30 mesh; 15% through 30 on 35 mesh; 17% through 35 on 40 mesh; 6% through 40 on 50 mesh; and 10% through 50 mesh on pan. Purity = 95%.
[2] Supplied by The J. M. Smucker Company; Red Raspberry Puree having 42.0° Brix.

This filling composition is prepared by a procedure analogous to the method of Example I. The resulting filling composition has an $A_w$ of about 0.253. A strawberry flavored filling composition of the present invention is prepared by substituting strawberry essence and strawberry puree for the raspberry essence and raspberry puree. This composition has an $A_w$ of about 0.305. Either of these fillings may be enrobed in chocolate.

Consumption of 15 grams (approximately 1 tablespoon) of one of these compositions by a person in need of laxation provides effective laxative benefits. These filling compositions, especially when enrobed in chocolate, are very convenient to use. The filling compositions have excellent palatability, mouthfeel, taste and texture, with the larger particle size psyllium giving the appearance and texture of a filling containing natural raspberry or strawberry seeds.

What is claimed is:

1. Psyllium-containing filling compositions having a non-gummy lubricious texture comprising, by weight of the composition:
   (a) from about 1% to about 50% of psyllium fiber;
   (b) from about 10% to about 75% of glycerin;
   (c) from about 0% to about 80% of at least one sweetener; and
   (d) from about 0% to about 10% of at least one flavorant;

and wherein further said composition is fluid and has an $A_w$ of 0.35 or less to avoid substantial gelation of the components of said composition such that the composition has a non-solid and non-gummy texture.

2. Psyllium-containing filling composition according to claim 1 comprising an artificial sweetener as part or all of the sweetener.

3. Psyllium-containing filling composition according to claim 1 comprising, by weight of the composition, in total from about 20% to about 65% of at least one sweetener.

4. Psyllium-containing filling composition according to claim 3 comprising sorbitol as part or all of the sweetener.

5. Psyllium-containing filling composition according to claim 3 comprising, by weight of the composition, from about 0.1% to about 7% of at least one flavorant.

6. Psyllium-containing filling composition according to claim 5 comprising, as part or all of the sweetener, from about 5% to about 30% sorbitol by weight of the composition.

7. Psyllium-containing filling composition having a non-gummy lubricious texture comprising, by weight of the composition:
   (a) from about 5% to about 40% of psyllium fiber;
   (b) from about 10% to about 50% of glycerin;
   (c) from about 20% to about 65% of at least one sweetener; and
   (d) from about 0.1% to about 7% of at least one flavorant;

and wherein further said composition is fluid and has an $A_w$ within the range of from about 0.05 to about 0.3 to avoid substantial gelation of the components of said composition such that the composition has a non-solid and non-gummy texture.

8. Psyllium-containing filling composition according to claim 7 comprising, as part or all of the sweetener, from about 5% to about 30% sorbitol by weight of the composition.

9. Psyllium-containing filling composition having a non-gummy lubricious texture comprising, by weight of the composition:
   (a) from about 20% to about 35% of psyllium fiber;
   (b) from about 10% to about 25% of glycerin;

(c) from about 40% to about 55% of at least one sweetener; and
(d) from about 0.1% to about 7% of at least one flavorant;
and wherein further said composition is fluid and has and $A_w$ within the range of from about 0.05 to about 0.3 to avoid substantial gelation of the components of said composition such that the composition has a non-solid and non-gummy texture.

10. Psyllium-containing filling composition according to claim 9 comprising, as part or all of the sweetener, from about 10% to about 25% sorbitol by weight of the composition.

11. Psyllium-containing filling composition according to claim 10 in the form of a sandwich cookie, said cookie comprising said filling composition sandwiched between two cookie basecakes, wherein said basecakes have an $A_w$ of less than about 0.3.

12. Psyllium-containing filling composition according to claim 10 having an $A_w$ within the range of from about 0.1 to about 0.25.

* * * * *

UNITED STATES PATENT OFFICE
CERTIFICATE OF CORRECTION

PATENT NO. : 5,143,728

DATED : September 1, 1992

INVENTOR(S) : James Wilbur Cappel and Robert Daniel Rece

It is certified that error appears in the above-identified patent and that said Letters Patent is hereby corrected as shown below:

On title page, item [63], line 2, "Ser. No. 83,441" should be --Serial No. 93,441--.

Item [56]
In the References Cited under U.S. Patent Documents --4,143,163 3/1979 Hutchinson et al 426/96-- was omitted.

In the References Cited under Foreign Patent Documents the following were omitted:
--2050142   1/1981  Great Britain--
--0166824   1/1986  European Patent Office--
--0166825   1/1986  European Patent Office--
--0142601   5/1985  European Patent Office--
--1461347  11/1966  France--

In the Abstract, line 8 "cholestrol" should be --cholesterol--.

Column 1, line 7 "Ser. No. 07/083,441" should be --Ser. No. 07/93,441--.

Column 3, line 31 "indian" should be --Indian--.

Column 7, line 9 "Weight" should be --Weigh--.

Signed and Sealed this

Fifth Day of October, 1993

Attest:

BRUCE LEHMAN

Attesting Officer

Commissioner of Patents and Trademarks